US00PP24444P3

(12) United States Plant Patent
Brown

(10) Patent No.: US PP24,444 P3
(45) Date of Patent: May 13, 2014

(54) ***CALLISTEMON VIMINALIS* PLANT NAMED 'CV01'**

(50) Latin Name: *Callistemon viminalis*
Varietal Denomination: CV01

(76) Inventor: Graham Brown, Pennant Hills (AU)

( * ) Notice: Subject to any disclaimer, the term of this patent is extended or adjusted under 35 U.S.C. 154(b) by 90 days.

(21) Appl. No.: 13/506,936

(22) Filed: May 25, 2012

(65) Prior Publication Data

US 2012/0331604 P1 Dec. 27, 2012

Related U.S. Application Data

(60) Provisional application No. 61/519,689, filed on May 27, 2011.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Sam McCoy

(57) ABSTRACT

'CV01' is a distinctive variety of *Callistemon viminalis*, which is characterized by its combination of columnar shape, tall plant height, strong branching, short leaf blade, and stability and uniformity of traits through successive cycles of asexual propagation.

2 Drawing Sheets

Latin name of the genus and species: The Latin name of the genus and species of the novel variety disclosed herein is *Callistemon viminalis*.

Variety denomination: The inventive variety of *Callistemon viminalis* disclosed herein has been given the variety denomination 'CV01'.

BACKGROUND OF THE INVENTION

The present invention relates to a new and distinct perennial variety of *Callistemon viminalis*, which has been given the variety denomination of 'CV01'. Its market class is that of an ornamental tree or shrub. 'CV01' is intended for use in landscaping as a small tree or hedge shrub.

Parentage: The *Callistemon viminalis* variety 'CV01' was the result of a controlled pollination between seed parent *Callistemon viminalis* 'Captain Cook' (unpatented) and pollen parent un-named *Callistemon viminalis* in September 2005 at a commercial plant breeding facility in Cobbitty in the state of New South Wales, Australia. Seed were collected and germinated during 2006 and transplanted to the field in 10 cm pots in September of 2006. Initial selection took place in September 2009 based on the above stated criteria. In 2010 trials and evaluation continued including confirmation of DUS (Distinctness, Uniformity and Stability) and commercial propagation by cuttings. The cultivar was named 'CV01'.

Asexual Reproduction: 'CV01' is propagated asexually by division. The distinctive characteristics of the inventive 'CV01' variety are stable from generation to generation; clones of the variety produced by asexual reproduction maintain the distinguishing characteristics of the original plant.

SUMMARY OF THE INVENTION

'CV01' is a distinctive variety of *Callistemon viminalis* which is characterized by the combination of tall plant height, columnar shape, dense growth habit and both longer and wider leaves.

As a shrub form of *Callistemon*, 'CV01' has a tall, upright, columnar growth habit with an overall plant height of approximately 2 to 2.5 meters (unpruned), a width of approximately 1 to 1.5 meters (unpruned) and strong shoot density. 'CV01' has a medium leaf length (35 to 45 mm) and a broad width.

BOTANICAL DESCRIPTION OF THE PLANT

Figure 1:
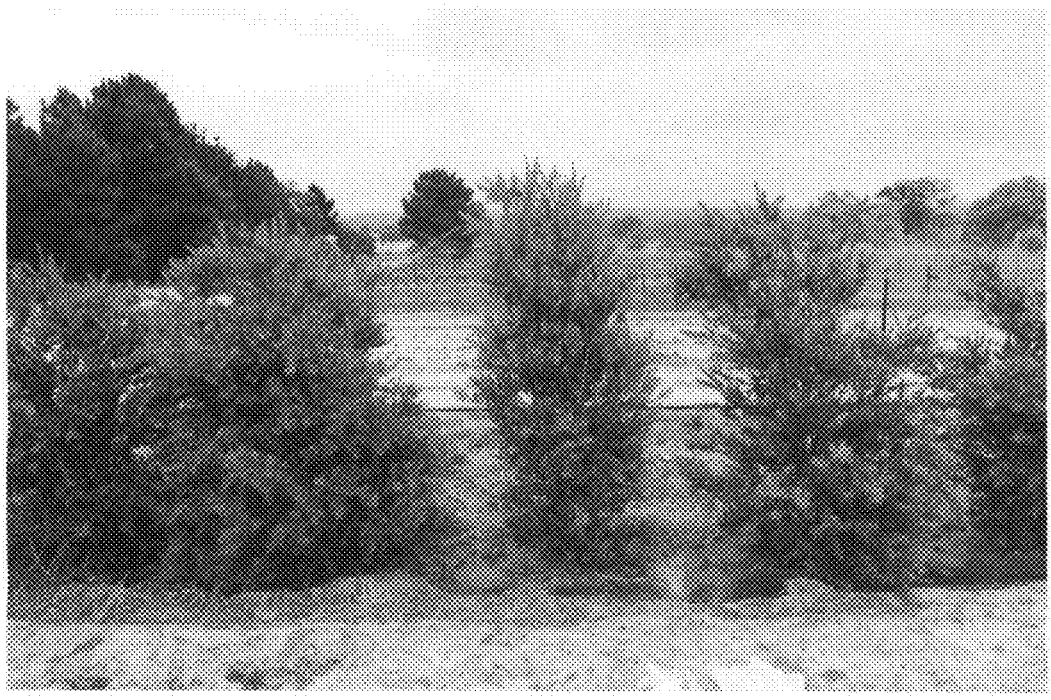
FIG. 1 shows a 'CV01' plant (center), in the ground and unpruned, at approximately 3 years old with other F1 seedling accessions from the same parent cross for comparison.
Figure 2:
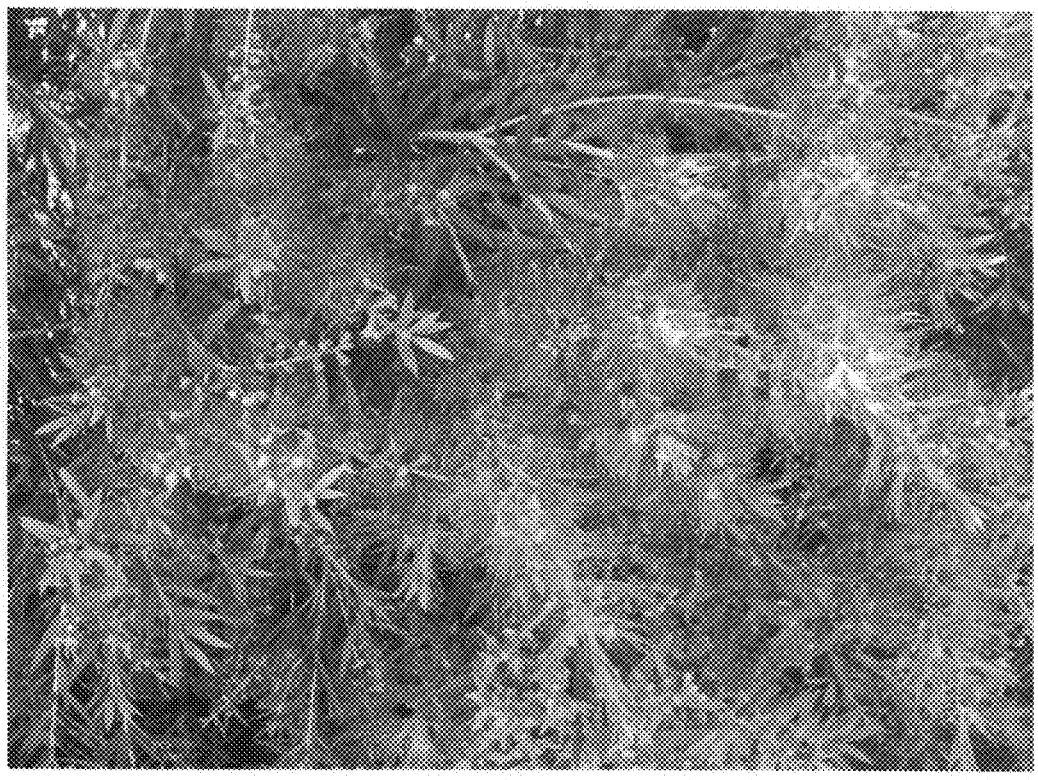
FIG. 2 shows a typical inflorescence spike

The following is a detailed botanical description of a new and distinct variety of *Callistemon viminalis* known as 'CV01' based upon observations of 24-month old plants grown from rooted cuttings into 200 mm nursery pots in full sun in open beds in Clarendon, New South Wales, Australia during spring 2009-summer 2010. Plant observations and descriptions were taken in summer 2010.

Those skilled in the art will appreciate that certain characteristics will vary with older or, conversely, with younger plants. 'CV01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition.

In southern climates, corresponding approximately to USDA Hardiness Zones 8 through 11, 'CV01' is an evergreen perennial *Callistemon viminalis*. 'CV01' is an upright, fastigate plant, with short and broad leaf blades and a dense growth habit.

A botanical description of 'CV01' and comparisons with other varieties of *Callistemon viminalis* are provided below.

Technical Description of the Variety.

Plant characteristics: Growth habit fastigiate, height tall (average foliar height in a 200 mm pot 110 cm), narrow width (average width 45 cm) shoot density strong.

Stems: Strong branching habit, branch angles acute. Shape is cylindrical with a smooth and corky texture, greyed red in color (approximately RHS 178C). Multi-branched primary stems arise very near soil level and the plant's base and exhibit a near vertical attitude with the longest measuring 100 cm long and 2.5 cm in diameter near the base. Immature stems are highly pubescent while mature stems are lightly pubescent to glabrous. Internode length ranges from 10 to 20 mm. Secondary branches arise freely at nodes; branch angles are acute and the attitude is erect. Immature color, mature color and internode length of the secondary branches correspond to the colors and internode length of primary stems.

Leaves: The simple leaves are sessile and absent of stipules, arrangement is whorled. Shape is lanceolate, margins entire, apex acute, base acute, venation pinnate with upper and lower surface color green corresponding to RHS 137B. Leaf texture in all stages is smooth and glabrous to finely pubescence. Immature leaves, upper and lower side color greyed green approximately RHS 174B. Mature leaves length medium with an observed length of 42 mm (average 37.4 mm) and observed width of 8 mm (average 7.4 mm). Color of both the upper and lower mature leaf surfaces are (RHS 137B).

Flowers and fruiting: Flowering characteristics of 'CV01' are very similar in nature to that of seed parent, 'Captain Cook': red bottlebrush flowers that almost completely obscure the foliage in spring.

Inflorescence: Oblong, cylindrical spikes approximately 8 to 10 cm long and 4.5 to 5.5 cm wide, comprised of many small sessile flowers with exserted stamen.

Bud: Many tightly grouped oblong or ovoid axillary buds measuring approximately 7 mm long and 3 mm wide prior to bud swell. Color approximates to yellow-green 146C, prior to bud swell.

Flowers: Sepals are immeasurably minute; corolla comprised of five petals; ovate. Color approximates to yellow-green (RHS 154C or 154D). No fragrance. Blooming is heaviest from spring to early summer and sporadic in autumn.

Reproductive organs: Stamens number approximately 50 to 60. Predominant color of exserted stamens red (RHS 53B). Observed length of 20 to 22 mm (average length is 21.4 mm) and very thin in diameter (less than 1 mm). Each stamen joins floral tube independently: Free. Anthers are minute and yellow in color; pollen is present. One pistil, measuring approximately 18 mm in length and less than 1 mm wide. Pistil color is red 53B. Ovary is half-Inferior.

Fruit and seed production: Dehescent flowers reveal round, slightly oblong seed capsules grouped tightly along the stem. Sessile. Dimensions are 3 to 5 mm in diameter and 4 to 5 mm in length. Color at maturity approximates to brown 200A. Seeds are many and minute with a color close to greyed orange 166B.

Cold and heat tolerance: 'CV01' has cold and heat tolerance typical of *Callistemon viminalis*.

Drought tolerance: 'CV01' has good drought tolerance typical of *Callistemon viminalis* once established.

Pest resistance: No known insect pests. 'CV01' has disease tolerance typical of *Callistemon viminalis*.

Cultural conditions: 'CV01' is tolerant of a wide range of soil types and pH ranges.

Comparisons with other *Callistemon*

As a shrub form of *Callistemon*, 'CV01' is better suited for hedge and patio garden applications as compared with the seed parent, *Callistemon viminalis* 'Captain Cook'. 'CV01' is characterized by a tall, upright and columnar growth habit with an overall plant height of approximately 2 to 2.5 meters (unpruned), a width of approximately 1 to 1.5 meters (unpruned) as compared with 'Captain Cook' which has a medium height and a semi upright to spreading habit with a height of approximately 1.5 to 2 meters (unpruned), a width of approximately 2 meters. 'CV01' has a strong shoot density and retains this density at maturity whereas 'Captain Cook' has a medium shoot density with a more open habit once mature. 'CV01' has a medium leaf length (35 to 45 mm) whereas *Callistemon viminalis* 'Captain Cook' has a long leaf length (50 to 60 mm). At a mean width of 7.4 mm, the leaves of 'CV01' are slightly wider than those of *Callistemon viminalis* 'Captain Cook' which on average have a width of approximately 6 mm.

The characteristics of 'CV01' are unusual for *Callistemon viminalis*, as these plants usually have a semi upright, spreading or weeping habit. There have been no other varieties of this species, known to the Inventor, selected to date with a growth habit similar to that of 'CV01'.

That which is claimed is:

1. A new and distinct variety of *Callistemon viminalis* plant named 'CV01', substantially as described and illustrated herein.

* * * * *